US007025994B1

(12) United States Patent
Briskin

(10) Patent No.: US 7,025,994 B1
(45) Date of Patent: Apr. 11, 2006

(54) DIETARY COMPOUNDS USEFUL FOR THE REDUCTION OF PATHOLOGICAL CONDITIONS AND THE PROMOTION OF GOOD HEALTH

(76) Inventor: Robert A. Briskin, 1004 S. Old Dixie Hwy., Suite 203, Jupiter, FL (US) 33458-7149

( * ) Notice: Subject to any disclaimer, the term of this patent is extended or adjusted under 35 U.S.C. 154(b) by 0 days.

(21) Appl. No.: 10/278,058

(22) Filed: Oct. 21, 2002

Related U.S. Application Data

(63) Continuation of application No. 09/881,482, filed on Jun. 14, 2001, now abandoned, which is a continuation of application No. 09/481,035, filed on Jan. 11, 2000, now abandoned.

(60) Provisional application No. 60/115,395, filed on Jan. 11, 1999.

(51) Int. Cl.
*A61K 35/78* (2006.01)

(52) U.S. Cl. .................................................... 424/725
(58) Field of Classification Search .................. 424/725
See application file for complete search history.

(56) References Cited

U.S. PATENT DOCUMENTS

| | | | |
|---|---|---|---|
| 4,206,221 A | 6/1980 | Miller et al. | |
| 4,478,855 A | 10/1984 | Dahlen et al. | |
| 4,857,326 A | 8/1989 | Stitt | |
| 4,888,187 A | 12/1989 | Given, Jr. et al. | |
| 4,906,457 A | 3/1990 | Ryan | |
| 4,960,790 A | 10/1990 | Stella et al. | |
| 4,992,282 A | 2/1991 | Mehansho et al. | |
| 5,157,049 A | 10/1992 | Haugwitz et al. | |
| 5,616,355 A | 4/1997 | Haast et al. | |
| 5,858,365 A | 1/1999 | Faller | |
| 5,876,782 A | 3/1999 | Saes et al. | |

OTHER PUBLICATIONS

Botting et al., Food and Chemical Toxicology, 37, 1999, 95-103.*
Barua, Biochem. J., 1999, 339, 359-362.*
Adams-Campbell et al., Ethnicity and Disease, 1993, 3 Suppl., S62-S66.*
Ben-Amotz et al., Food Chemistry, vol. 62, No. 4, pp. 515-520, 1998.*
Muanza et al., *International Journal of Pharmacognosy* (1995), 33(2): 98-106.
Ben-Amotz et al., *Food Chemistry* (1998), 62(4): 515-520.
Wei et al., *Journal of the Chinese Agricultural Chemistry Society* (1995), 33(3): 355-362.
Adams-Campbell et al., *Ethnicity and Disease* (1993), 3 Suppl., S62-6.
Le Marchand et al., "An Ecological Study of Diet and Lung Cancer in the South Pacific", *Int. J. Cancer* (1995), 63:18-23.
Le Marchand et al., "Vegetable Consumption and Lung Cancer Risk: A Population-Based Case-Control Study in Hawaii", *J. of the Nat. Cancer Inst.* (1989), 81(15): 1158-1164.
Franke et al., "Inhibition of Neoplastic Transformation and Bioavailability of Dietary Flavonoid Agents", *Advances in Experimental Medicine and Biology* (1998), 439: 237-248.
Moon, "Comparative Aspects of Carotenoids and Retinoids as Chemopreventive Agents for Cancer", *J. Nutr.* (1989), 119: 127-134.
Hong et al., "Prevention of Second Primary Tumors with Isotretinoin in Squamous-Cell Carcinoma of the Head and Neck", *The New England J. of Medicine* (1990), 323: 795-800.
Alfthan et al., "Tigason® (Etretinate) in Prevention of Recurrence of Superficial Bladder Tumors", *Eur. Urol.* (1983), 9: 6-9.
Nashino, "Cancer Prevention by Natural Carotenoids", *J. Cell Biochem.* (1997), Suppl. 27: 86-91.
Nashino, "Cancer Chemoprevention by Natural Carotenoids and Their Related Compounds", *J. Cell Biochem.* (1995), Suppl. 22:231-235.
Rowinsky and Donehower, "Review Article: Drug Therapy", *New England J. of Medicine* (1995), 332(15): 1004-1014.
Minale et al., *Fortschr. Chem. Org. Naturst.* (1976), 33:1-72.
Schiff et al., "Promotion of Microtubule Assembly In Vitro by Taxol", *Nature* (1979), 22: 665-667.
Fuchs and Johnson, "Cytologic Evidence that Taxol, an Antineoplastic Agent from *Taxus brevifolia*, Acts as a Mitotic Spindle", *Cancer Treat. Rep.* (1978), 62: 1219-1222.

(Continued)

*Primary Examiner*—Michael Meller
(74) *Attorney, Agent, or Firm*—Saliwanchik, Lloyd & Saliwanchik

(57) ABSTRACT

The subject invention provides compositions useful for the promotion of good health in humans and animals. In a preferred embodiment, these compositions contain extracts from mangos. The compositions may be pills, bars, drinks or other dietary supplement.

4 Claims, No Drawings

OTHER PUBLICATIONS

Faulkner, "Marine Natural Products", *Natural Products Reports* (1987), 4(5): 539-576.

Uemura, et al., *J. Am. Chem. Soc.* (1985), 107: 4796-4798.

Mir et al., *Journal of Food Engineering* (1995), 25: 141-150.

* cited by examiner

DIETARY COMPOUNDS USEFUL FOR THE REDUCTION OF PATHOLOGICAL CONDITIONS AND THE PROMOTION OF GOOD HEALTH

CROSS-REFERENCE TO RELATED APPLICATIONS

This application is a continuation of patent application U.S. Ser. No. 09/881,482, filed Jun. 14, 2001 now abandoned; which is a continuation of Ser. No. 09/481,035, filed Jan. 11, 2000 now abandoned; which claims priority from provisional patent application U.S. Ser. No. 60/115,395, filed Jan. 11, 1999.

BACKGROUND OF THE INVENTION

From the beginning of recorded time people have made efforts to promote good health in humans and animals. The efforts to promote good health include the identification of compositions such as drugs which treat diseases. However, a preferable approach is to identify preventative measures which reduce the likelihood of pathological conditions. In this regard it is particularly advantageous to identify preventative methods which can be readily practiced by all people without side effects. Unfortunately, such beneficial preventative measures have proven to be very illusive, as evidenced by the high incidence of cancer, heart disease and other pathologies in our society.

For many years now, considerable research and resources have been devoted to the study of oncology and the identification and development of materials and methods for the control of cancer. The methods which have been investigated include radiation, chemotherapy, herbal medicines and holistic approaches. While certain methods and chemical compositions have been developed which aid in inhibiting, remitting, or controlling cancer, new methods and anticancer chemical compositions are needed.

In searching for new biologically active compounds, it has been found that some natural products and organisms are potential sources for chemical molecules having useful biological activity. For example, the diterpene commonly known as taxol, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature* (London) 22:665–667). Taxol is also known to have antitumor properties and has undergone a number of clinical trials which have shown it to be effective in the treatment of a wide range of cancers (Rowinski, E. K. R. C. Donehower [1995] *N. Engl. J. Med.* 332:1004–1014). See also, e.g., U.S. Pat. Nos. 5,157,049; 4,960,790; and 4,206,221.

Marine sponges have also proven to be a source of biologically active chemical molecules. A number of publications have been issued disclosing organic compounds derived from marine sponges including Scheuer, P. J. (ed.) *Marine Natural Products, Chemical and Biological Perspectives*, Academic Press, New York, 1978–1983, Vol. I–V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72; Faulkner, D. J. (1987) *Natural Products Reports* 4:539–576, and references cited therein.

The role of diet in maintaining optimal health in a subject, and in slowing or reversing the progression of disease has been the subject of much public attention and commercial enterprise. The term "nutriceutical" is intended to describe specific chemical compounds found in foods that may prevent disease. The term "phytochemical" emphasizes the plant source of most of these protective, disease-preventing compounds. Relatively little is known about the biological effects of phytochemicals, but it is widely believed that this group of compounds will assume a role similar to common multi-vitamins in the future. Where data is available, it is usually derived from long-term epidemiological studies of humans, or studies in animals with diet regimens. Current studies are showing that as we move away from the diet of our ancestors we succumb to modern diseases. Evidence for this is seen in societies that live in remote villages and who still embrace traditional dietary practices yet remain relatively free of modern diseases, such as cancer.

For example, epidemiological studies strongly suggest a protective role for diet rich in fruits and vegetables against lung cancer. Studies have shown a marked differential in the rates of lung cancer in the islands of the South Pacific, independent of cigarette smoking (Loic Le Marchland, et. al., (1989) "Vegetable consumption and Lung Cancer: A Population-Based Case-Control Study in Hawaii", *J. Natl. Cancer Institute,* 81:1158; and Loic Le Marchand, et. al., (1995) "An Ecological Study of diet and Lung Cancer in the South Pacific", *Int. J. Cancer:* 63:18). Consumption of a variety of fruits and vegetables is thought to partly explain this difference.

Dietary components such as soluble fibers and flavonoid agents have been suggested as having beneficial effects in reducing the risk of cancer (Franke, Adrian A., Robert V. Cooney, Laurie J. Custer, Lawrence J. Mordan, Yuichiro Tanaka (1988) "Inhibition of Neoplastic Transformation and Bioavailability of Dietary Flavonoid Agents" *Advances in Experimental Medicine and Biology* 439:237).

Retinoids have been shown to inhibit carcinogenesis in many experimental systems (Moon, R. C., (1989) "Comparative Aspects of Carotenoids and Retinoids as Chemopreventive Agents for Cancer", *J. Nutr.,* 119:127) and in humans, to prevent neoplasia (cancer) or to revert precancerous lesions at several anatomical sites (Hong, W. K., et al., (1990) "Prevention of Second Primary Tumors with Isotretinoin in Squamous Cell Carcinoma of the Head and Neck", *NEJM,* 323:795; and Alfthan, O., et. al., (1993) "Etretinate in Prevention of Recurrence of Superficial Bladder Tumors: A Double-blind clinical Trial", *Eur. Uro.,* 9:6).

Researchers have stated that various natural carotenoids, which co-exist with beta carotene in fruits and vegetables, have anti-carcinogenic activity, especially lycopene and lutein (Nishino, H., (1997) "Cancer Prevention by Natural Carotenoids", *J. Cell Biochem.* Suppl., 27:86 and "Cancer Chemoprevention by Natural Carotenoids and their Related Compounds", *J. Cel Biochem.* Suppl., 22:231). Carotenoids generally refer to a class of labile, easily oxidizable, yellow, orange, red, or purple pigments, which are lipid in character, and widely distributed in plants.

Some phytochemicals may be categorized as anti-oxidants, vitamins which neutralize free radicals (molecules with unpaired electrons). Free radicals attack cells and damage tissues resulting in premature aging, reduced immune function, inflammation and ultimately degenerative disease. The hydroxyl radical (OH•), an oxidizing agent produced by the degradation of hydrogen peroxide and molecular oxygen, is regarded as being the most damaging species. Aging and deterioration in human cells is caused by the chemical process of oxidation. Scientists theorize that when pollutants, chemicals, and toxins such as cigarette smoke or food additives combine with oxygen in the bloodstream, unstable free radicals are produced. Free radicals then weaken cell membranes, inviting disease and infection. Anti-oxidant nutrients, such as vitamin C and E, are the body's primary defense against free radicals. Anti-oxidants restrict the supply of oxygen to the free radicals, neutralizing them. Therefore, the cells and tissues remain younger and healthier.

The present invention has added to the arsenal of anti-cancer compositions by the discovery of organic compositions possessing anti-oxidant activities. These compositions can be isolated from extracts of mangos. Other health-promoting benefits of the compositions of the subject invention are set forth below with particularity.

BRIEF SUMMARY OF THE INVENTION

In one embodiment, the subject invention pertains to materials and methods useful for the inhibition of neoplastic transformation. Specifically, compositions which can be obtained from citrus can be used to inhibit or prevent pathological cellular proliferation. In a particularly preferred embodiment, the subject invention pertains to the use of compositions from mangos to treat neoplastic transformations associated with cancer. The compositions of the subject invention are particularly advantageous because they can be obtained from natural sources and are not known to be toxic.

In one embodiment, the present invention relates to reducing the incidence of cancer using a nutritional supplement comprising a mango extract. In a preferred embodiment, the compositions of the subject invention are used as part of a diet aimed at reducing the risk of cancer. Mango is an easily renewable and cost effective resource for the health-promoting compositions of the subject invention. Furthermore, the mango's unique carotenoid and hydrophilic extracts have very favorable properties in their ability to inhibit neoplastic transformation of cells.

In one embodiment, the subject invention provides compositions useful for the inhibition of neoplastic transformation. These compositions may be in the form of food or beverage products or may be formulated into a pharmaceutical composition. In a preferred embodiment, the compounds of the present invention may be formulated into an edible nutritive food bar.

In a further embodiment of the subject invention, methods are provided for inhibiting neoplastic transformation. In a preferred embodiment the inhibition of neoplastic transformation is used as a treatment for cancer. The methods and compositions of the subject invention can be applied to humans and to animals.

The compositions of the subject invention can be applied without other active ingredient or in conjunction with other active ingredients. The other active ingredient(s) may be, for example, other compounds which inhibit or prevent cancer.

DETAILED DISCLOSURE OF THE INVENTION

The subject invention pertains to the use of phytonutrients to promote good health in humans and animals. In a preferred embodiment of the subject invention, the phytonutrients are contained in extracts of mango fruit. In a particularly preferred embodiment, the phytonutrients are contained within the hydrophilic extract of the mango. Alternatively, the phytonutrients are contained within the lipophilic extract of the mango. The person skilled in this art, having the benefit of the current disclosure can readily formulate the phytonutrient extracts and compounds of the subject invention into a pill, bar (the "phytobar"), or other edible composition for easy and enjoyable consumption. These therapeutic compositions can be used as described herein to promote a healthy state thereby decreasing the incidence and/or severity of cancer, heart disease and other chronic illnesses. The compositions and methods of the subject invention are particularly advantageous due to their antioxidant properties.

In one embodiment, the present invention provides a nutriceutical compositions containing mango extracts. The mango hydrophilic and carotenoid extracts can be obtained using extraction processes known to those skilled in the art having the benefit of the instant disclosure. Procedures relating to the processing of citrus, including mangos, are well known to those skilled in the art and are described at, for example, Cano and de Ancos (Cano, M. Pilar and Begoña de Ancos (1994) "Carotenoid and Carotenoid Ester Composition in Mango Fruit As Influenced by Processing Method" *American Chemical Society* 42(12):2737–2738).

The present invention involves the use of the hydrophilic and/or lipophilic carotenoid extracts of mango to inhibit the neoplastic transformation of cells.

The nutritional supplement of the subject invention may contain the mango's extracts, in the appropriate doses, individually or a combined form. The nutritional supplement can take on various forms, including but not limited to pills, edible nutritional bars or nutritional drink or drink mix. The purpose is achieved by the nutritional supplement then becoming part of the daily diet. The compounds of the subject invention may be combined with other components such as, for example, a soluble fiber compound. The soluble fiber compound may be, for example, locust gum, guar gum, pectin, gum arabic, or psyllium.

The nutritional supplement of the subject invention can also be combined with all of the traditional vitamin supplements. For example, the nutritional supplement of the subject invention can be formulated with the following additional ingredients: vitamin A, vitamin A acetate, vitamin $B_1$, vitamin $B_2$, vitamin $B_6$, vitamin $B_{12}$, vitamin D, calcium panthotenate, niacinamide, copper, iodine, iron, magnesium, manganese, hydrochloride and selenium. The above metals can be incorporated either as the sulfates or as the carbonates.

Following are examples which illustrate procedures for practicing the invention. These examples should not be construed as limiting. All percentages are by weight and all solvent mixture proportions are by volume unless otherwise noted.

EXAMPLE 1

Formulation and Administration

The compositions of the invention are useful for various non-therapeutic and therapeutic purposes. Because of the antiproliferative properties of the compounds, they are useful to prevent unwanted cell growth in a wide variety of settings including in vitro uses. They are also useful as standards and for teaching demonstrations.

Therapeutic application of the new compositions can be accomplished by any suitable therapeutic method and technique presently or prospectively known to those skilled in the art.

When used to reduce the severity or incidence of cancer, the dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or an encapsulating material.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The nutriceutical supplement of the present invention can be in unit dosage form. In such form, the preparation is subdivided into unit doses containing appropriate quantities of the nutriceutically active component. The unit dosage form can be a packaged preparation, such as packeted tablets, capsules, lotions, ointments and powders in vials or ampoules. Also, the unit dosage can be a drink (such as a powder-based drink, shake or tea formulation), yogurt, solid food product, capsule, tablet, lotion, ointment, chewing gum, lozenge, or it can be the appropriate number of any of these in packaged form.

EXAMPLE 2

Food Bar Formulation

In a preferred embodiment, there is provided a dosage unit for the nutriceutical supplement of the present invention in the form of a food bar. The food bar, which may be cooked or non-cooked, may contain a grain or grains, nuts, possibly dried fruit, sweeteners and other ingredients that may be mixed with a binder, such as a sugar syrup or shortening, and formed into "bars" of desirable size. Generally, food bars are prepared in bar form of a manageable size for a product of this nature, and bearing in mind both package size and time required for consumption, weigh in the range of 2–3 ounces.

To provide an acceptable amount of nutrition, the food bar of the present invention may contain an amount of protein in addition to significant amounts of complex and simple carbohydrate, such as those non-cooked food bars described by U.S. Pat. No. 4,055,669. Further, the food bar of the present invention may contain dietary fiber to aid in the normalization of bowel function and reduce the risk of colonic diseases. There are presently available a number of non-cooked food bars that provide varying amounts of dietary fiber while possessing requisite qualities of acceptable taste and texture, including food bars described in U.S. Pat. Nos. 4,673,578 and 4,871,557. In addition to those anti-oxidants contained within the mango compound of the claimed invention, the food bar of the present invention may contain additional antioxidants of a source other than mango extract, such as described in U.S. Pat. No. 4,451,488. For example, the food bar of the present invention may contain one or more additional antioxidants, with each additional antioxidant selected from the group consisting of orange crystal, carrot juice powder, pineapple crystal, coriander seed, beet juice powder, barley grass powder, flax seed, hulled sesame seed, sunflower seed vitamin E oil, orange oil, lemon oil and sorghum syrup. The food bar of the present invention may contain lecithin, which has been reported to aid in digestion of fats and supplies choline, necessary for the production of the neurotransmitter acetylcholine. Food bars containing lecithin are described in U.S. Pat. No. 4,871,557.

EXAMPLE 3

Extraction of Health-promoting Components from Mango

Mango can be cut into pieces, preferably not bigger than 3 cm and freeze-dried. Weights before and after the drying process can be recorded. The mango composition can be homogenized using a mortar and pestle with about 0.2 g magnesium carbonate and about 2 g sodium sulfate. 25 mL tetrahydrofuran (THF) containing 0.025% butylated hydroxytoluene (BHT) to prevent oxidative degradation can be added, and the mixture extracted by thorough grinding. The liquid can be separated from the solids by centrifugation and the solids re-extracted according to this procedure with 25 mL portions of THF until the THF phase is decolored.

Aliquots of the combined THF extract can be dried under reduced pressure at room temperature and redissolved in hexane in a separatory funnel followed by partitioning between water containing about 13 g NaCl/L and hexane at least three times.

The organic phase (solid component) isolated after centrifugation can be dried over sodium sulfate and the volume of the water-free solution dried under reduced pressure at room temperature. This residue can be dissolved by short sonication in THF and used in assays on health products.

The aqueous phase (liquid component) can be freeze-dried and dissolved by short sonication in assay media or mixed with other components to prepare a desired product.

EXAMPLE 4

Evaluation of Mango Extract for Health-promoting Components

An in vitro transformation assay may be conducted using cells treated with mango extract and compared with that of a control. As is known by one of ordinary skill in the art, malignant transformation of a cell may be recognized in tissue culture, (a) by cells piling up on the bottom of the culture dish to form a focus; (b) by growth anchorage-independent conditions in semisolid media such as methylcellulose or agar; or (c) by tumor formation in syngeneic or immune-deprived animals.

A variety of fresh explants of cells and established cell lines are available to assay malignant cell transformation in vitro, such as the 10T1/2 cell line isolated from $C_3H$ mouse embryos and the 3T3 cell line derived from Balb/C mouse embryo fibroblasts. Typically, such cell lines are immortal but undergo normal contact inhibition, i.e., when cells come in close proximity to one another, they stop dividing but remain viable. Therefore, untransformed cells cultured in flasks or petri dishes will form a contact-inhibited monolayer. In addition, if fibroblasts are grown in a flask, they are anchorage dependent, i.e., will not grow in suspension.

Transformed foci may be induced by exposure to radiation or a chemical carcinogen, such as benzo(a)pyrene, benzidine, vinyl chloride, N-nitrosodimethylamine, cycasin, aflatoxin $B_1$ or 3-methylcholanthrene (MCA). Surviving cells are then left to grow to confluency, which requires several divisions. At this time, no foci are seen seen but if the dishes are held with appropriate media changes for 4–6 weeks after confluency is obtained, discrete foci of transformed cells can be counted after appropriate staining of the dishes. These foci are identified by their dense, multilayered structure, basophilic staining, and the random orientation of the spindle-shaped cells. The frequency of transformation can be expressed as the number of foci per surviving cell or number of foci per dish or flask.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for treating cancer by inhibiting neoplastic transformation comprising orally administering a nutriceutical composition comprising hydrophilic aqueous extract of mango fruit to a human or animal in need thereof.

2. The method, according to claim 1, wherein said composition is formulated into a food preparation.

3. The method, according to claim 2, wherein said food preparation is a food bar.

4. The method, according to claim 1, wherein said extract is freeze-dried.

* * * * *